(12) United States Patent
Cane'

(10) Patent No.: US 6,447,487 B1
(45) Date of Patent: Sep. 10, 2002

(54) APPARATUS FOR ADMINISTERING DRUGS TO A PATIENT

(75) Inventor: Mario Cane', Collegno (IT)

(73) Assignee: Cané S.R.L., Rivoli (IT)

( * ) Notice: Subject to any disclaimer, the term of this patent is extended or adjusted under 35 U.S.C. 154(b) by 0 days.

(21) Appl. No.: 09/562,145

(22) Filed: May 1, 2000

(51) Int. Cl.[7] .................................................. A61M 1/00
(52) U.S. Cl. ........................ 604/181; 604/187; 604/154; 604/131
(58) Field of Search ................................. 604/181, 110, 604/195, 228, 154, 131, 187

(56) References Cited

U.S. PATENT DOCUMENTS

| | | | | |
|---|---|---|---|---|
| 2,832,340 A | * | 4/1958 | Dann et al. | 604/228 |
| 3,253,592 A | * | 5/1966 | Von Pechmann | 604/222 |
| 3,880,138 A | * | 4/1975 | Wootten et al. | 604/507 |
| 4,493,703 A | * | 1/1985 | Butterfield | 604/110 |
| 4,677,980 A | * | 7/1987 | Reilly et al. | 604/228 |
| 5,062,832 A | * | 11/1991 | Seghi | 604/218 |
| 5,304,150 A | * | 4/1994 | Duplan et al. | 604/110 |
| 5,330,440 A | * | 7/1994 | Stanners et al. | 604/110 |
| 5,383,858 A | * | 1/1995 | Reilly et al. | 604/187 |

* cited by examiner

*Primary Examiner*—Edward K. Look
*Assistant Examiner*—Richard Woo
(74) *Attorney, Agent, or Firm*—Notaro & Michalos PC

(57) ABSTRACT

An infusion apparatus for administering drugs to a patient has a threaded shaft acting on a plunger of a syringe and is provided with protection against overdose caused by free flow. The protection is in the form of an adapter connected to the threaded shaft and having a neck and head with roughened surface extending into a threaded seat in the plunger.

6 Claims, 3 Drawing Sheets

APPARATUS FOR ADMINISTERING DRUGS TO A PATIENT

FIELD OF THE INVENTION

The present invention relates to an apparatus for delivering intravenous drugs to a patient.

More particularly the invention is concerned with a drug infusion apparatus provided with a protection against drug overdose that could occur because of a free and uncontrolled delivery flow of the liquid drug from the apparatus to the patient.

BACKGROUND OF THE INVENTION

A presently known infusion apparatus provides for electromechanical devices capable of applying a slow and progressive motion to a slider that in turn moves a plug in a plastic syringe, this latter being either of conventional design or purposely designed for liquid drug infusion.

These devices generally comprise a threaded shaft connected to a slider actuating the syringe plunger for injecting a drug into the patient through a small hose terminating with a needle that is permanently inserted under the skin.

An apparatus of this type is disclosed in Italian Utility Model No. 193915. In accordance with the teaching of Italian Utility Model No. 193915 a portable apparatus for delivering insulin to a patient comprises a housing for a conventional syringe, a slider acting on the syringe plunger, a threaded shaft for advancing the slider, an electric motor for rotating, the threaded shaft and an electronic control unit for controlling the apparatus operation.

A drawback of the apparatus disclosed by Utility Model No. 193915 comes from the fact that such apparatus results in being rather awkward and therefore unsuitable for portable use when it is realized for syringes capable of delivering drug amounts in the order of 20 cc. and larger, for example of the type used in ferro-chelating therapy.

To overcome the above discussed drawback, several devices have been proposed, one of them being disclosed in Italian patent application No. T092A000561 in the name of the present applicant.

The drug infusion device according to the above mentioned patent application comprises a pushing member or pusher made up by an axially movable threaded shaft for operating the syringe (plunger).

To this pusher there is directly fitted the plunger of a syringe filled with the drug to administer.

To this purpose the syringe is equipped with a removable stem that is used for sucking the drug and is then removed.

The device realized according to Italian patent application No. T092A000561 has a smaller size and can be used as a portable device.

However the above mentioned device has the shortcoming of a poor seal between the pusher and the syringe plunger which under certain circumstances could lead to the detachment of the pusher from the plunger.

More particularly, when for any reason the apparatus with the syringe containing the liquid is located a few tens of centimeters above the needle inserted under the skin, a drug can be delivered to the patient at an uncontrolled rate ("free flow").

Such uncontrolled rate flow is substantially caused by the pressure difference in the syringe due to the height difference between the syringe and the point at which the under-the-skin needle is located.

Thus a pressure difference (or overpressure) caused by the liquid column in the hose is present at the end near the needle.

Such pressure difference causes a larger downflow of the liquid and creates a lower pressure in the syringe chamber.

The resulting effect is further enhanced by the diameter difference between the hose and the syringe. Such lower pressure applied to the syringe plunger surface generates a force strong enough to attract the plunger and cause its detachment from the pusher. This way an uncontrolled or free flow of liquid is created that can cause a drug overdose resulting in serious trouble for the patient.

In this regard it is pointed out that in some countries the infusion devices are subjected to tests comprising a check of the protection degree ensured by the device against the free flow drawback.

It is therefore an object of the present invention to provide an apparatus for infusing drugs that is not affected by a free (uncontrolled) flow of liquid when a drug is being administered to a patient.

Another object of the present invention is to provide an infusion apparatus in which the syringe plunger can be easily fitted to the pusher and without causing slippages of the plunger that could cause drug leakages.

SUMMARY OF THE INVENTION

The above and other objects of the invention are achieved through an apparatus for drug infusion as claimed in the attached claims.

The present invention provides for mechanically locking the syringe plunger thanks to the elasticity of a plunger made of rubber for ensuring a proper seal in the plunger-pusher connection.

The above mentioned objects of the invention will become clear from the following detailed description of an embodiment thereof with particular reference to the attached drawings in which:

DESCRIPTION OF THE PREFERRED EMBODIMENT

Figure 1:
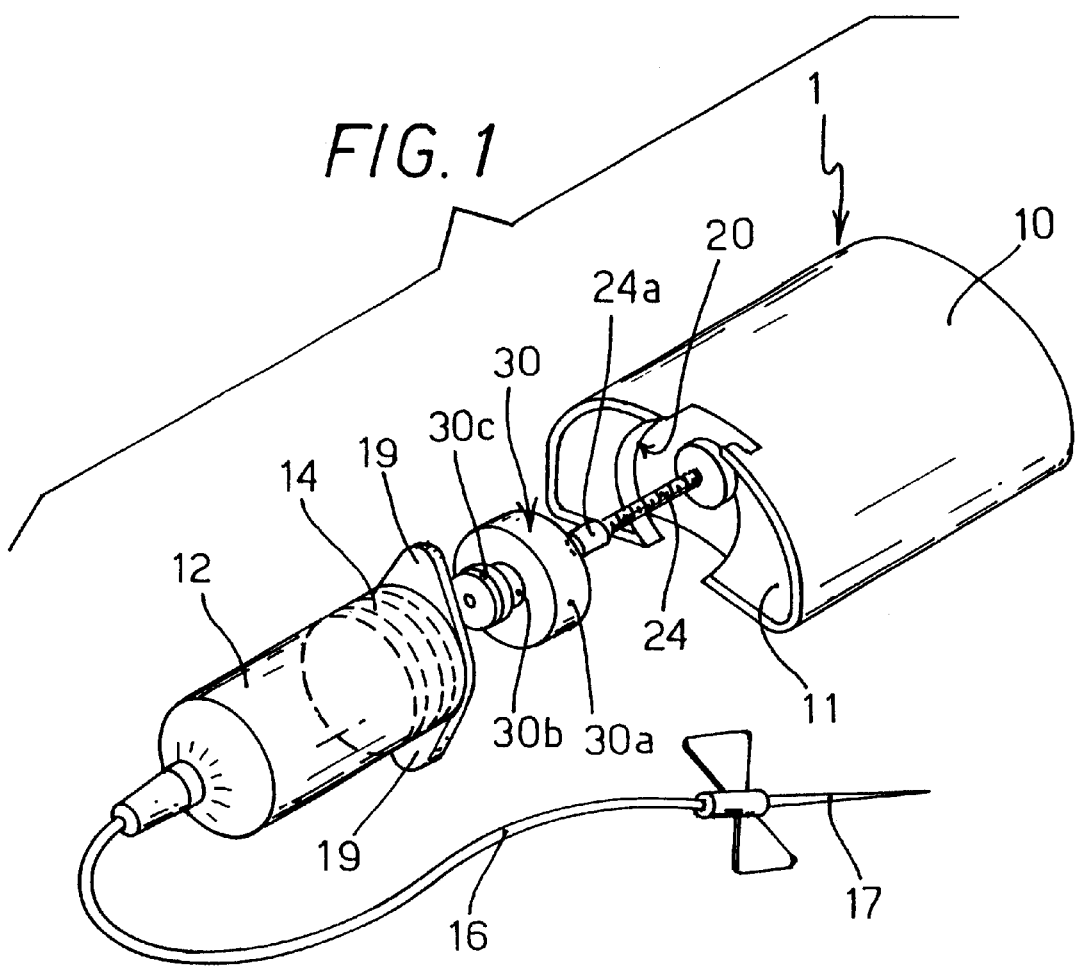
FIG. 1 is a perspective exploded view of an infusion apparatus according to the invention.
Figure 2:
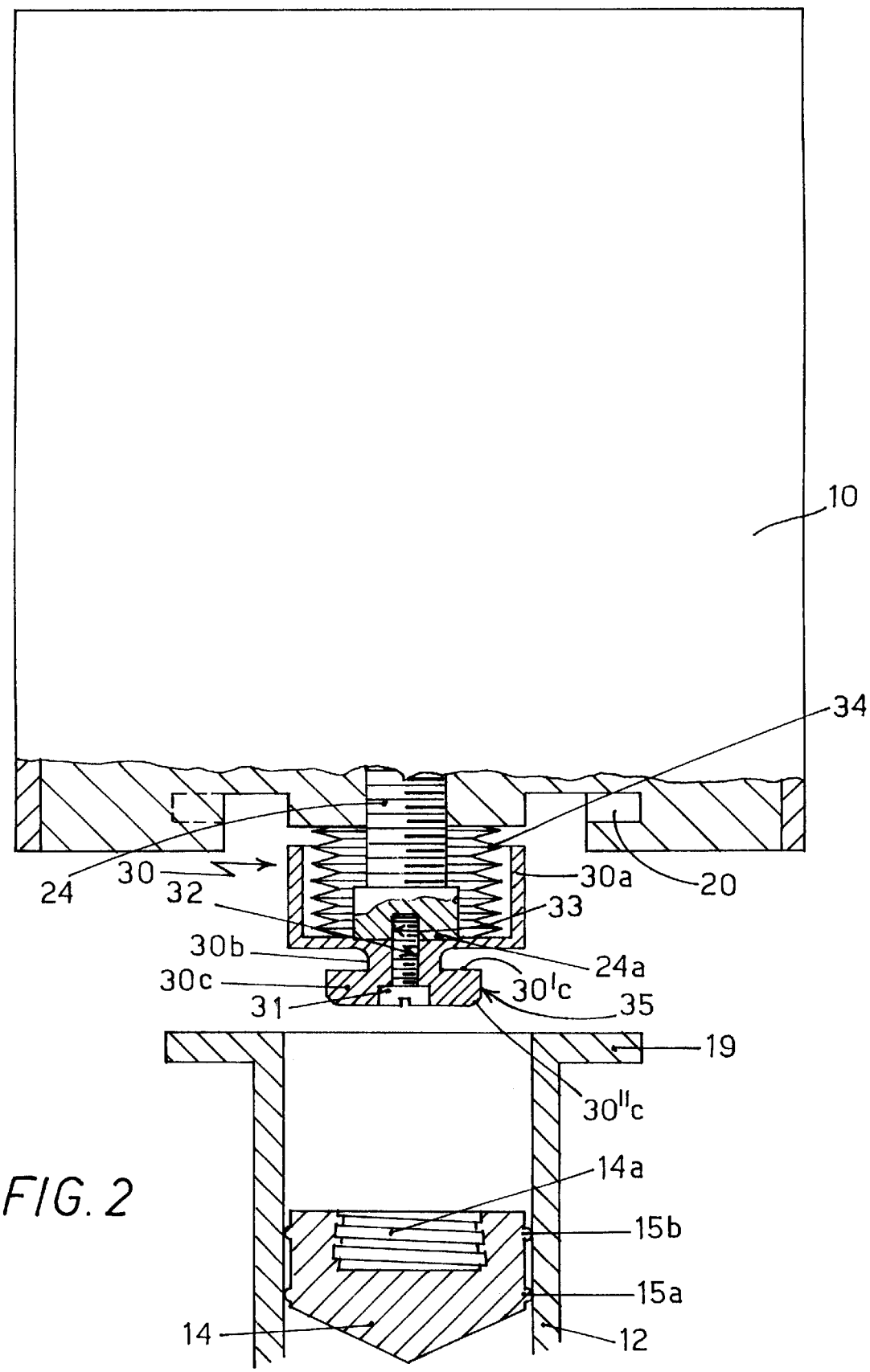
FIG. 2 is a front section scrap view of the apparatus according to the invention.

With reference to FIGS. 1 and 2 an infusion apparatus 1 according to the invention is shown, such apparatus comprising a housing 10 having a suitable anatomical shape and being closed by a cover 11 to which a syringe 12 containing the drug can be fitted.

In order to make the apparatus portable, means are fastened to the housing 10, such as a strap for wearing the apparatus on the arm or a clip for securing the apparatus to the belt of a patient (such means are not shown in the drawings since they are well known).

Syringe 12 is provided with a piston or plunger 14 and is connected by a small hose 16 to a needle 17 permanently inserted under the skin of a patient for parentally injecting predetermined amounts of a drug.

Figure 3:
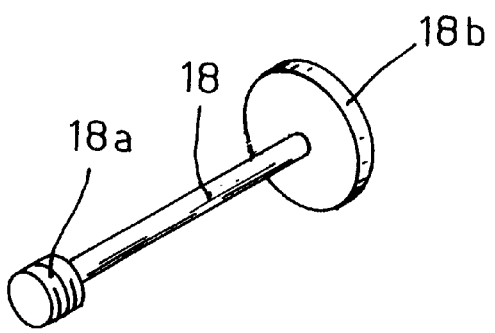
FIG. 3 is a perspective view of a stem for a syringe.
Figure 4:
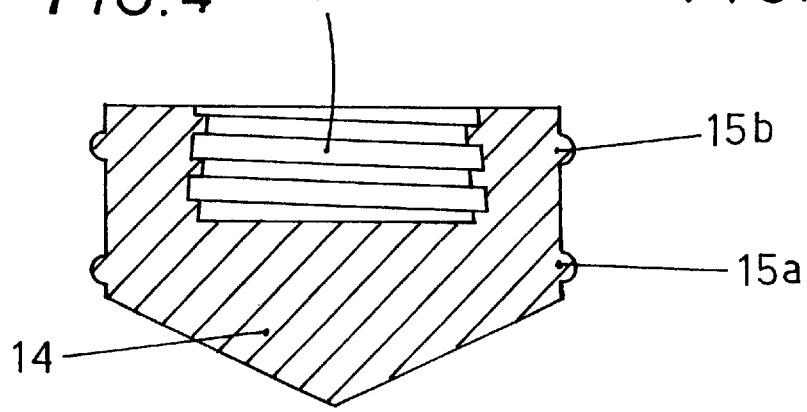
FIG. 4 is a front section view of a plunger for syringe.

As shown in FIGS. 3 and 4, the plunger head 14 is of rubber and is provided with an inner thread 14a on which a correspondingly threaded end portion 18a of a stem 18 is removably screwed, the stem being further provided with a handle 18b at the other end portion.

The removable stem 18 is used for moving the plunger head 14 to draw the drug and is later removed so that the filled syringe 12 can be fitted to the infusion apparatus 1.

To ensure a proper seal between the plunger head 14 and the syringe 12 during their relative motion, annular projections are formed on the side surface of the plunger 14, namely a projection 15a near the end facing the liquid and a projection 15b near the outer end of the plunger head.

The inner diameter of the syringe 12 is slightly smaller than. the diameter of the plunger head plus the projections 15a, 15b so that these latter are deformed when the parts are assembled, thus ensuring a proper sealing that prevents liquid leakages.

Returning to FIGS. 1 and 2, in order to lock the syringe 12 to the apparatus 1 the holding means usually provided on such syringes are used, such means comprising projecting tabs 19 that engage corresponding grooves 20 formed in the cover 11 to form a bayonet connection.

A threaded shaft 24 is rotated by an electric actuator such as a motor reducer and actuates (moves) the plunger head 14 of the syringe 12.

The portion of the threaded shaft 24 projecting from the apparatus has a cylindrical end 24a.

An adapter 30 adapted for being inserted into the seat 14a formed in the plunger head 14 is fastened to said cylindrical end, and provides a protection against the above mentioned conditions of free flow of liquid from the syringe.

Figure 5:
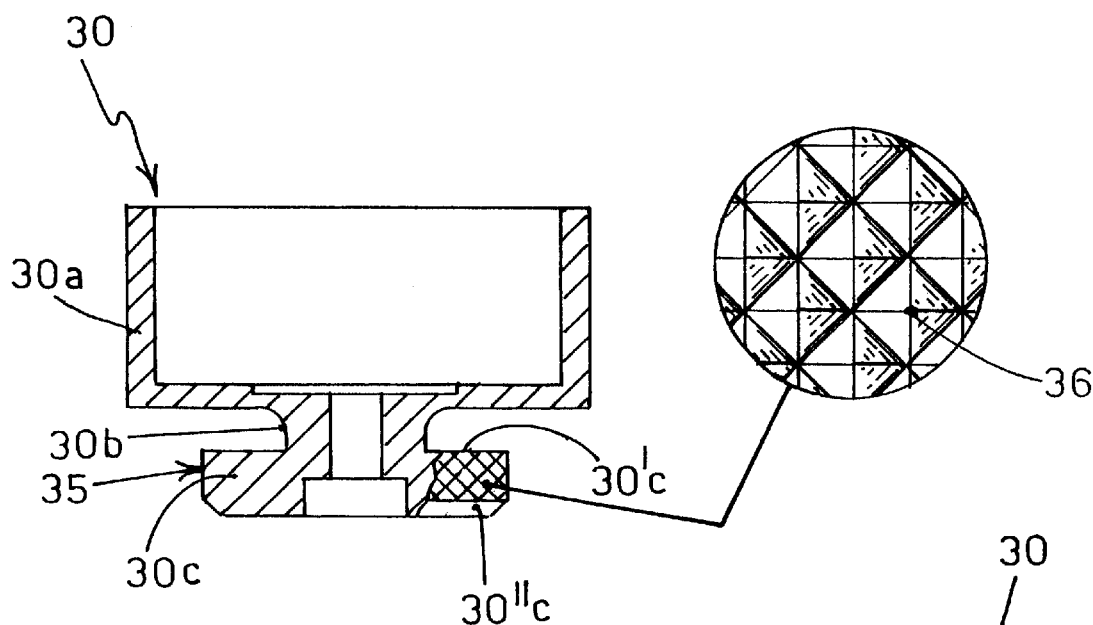
FIG. 5 is a front section view of a detail of the apparatus according to the invention.

Referring also to FIG. 5, the adapter 30 comprises a cylindrical hollow body 30a and a neck portion 30b terminating with a head member 30c both having a generally cylindrical shape.

The free end of head member 30c has a circumferential tapering 30"c along its whole edge for making easier the insertion of the adapter 30 into the plunger head 14, whereas the opposed end of the head member has a substantially flat base 30'c blending with the neck portion 30b.

Numeral reference 35 indicates the side surface of the head member 30c.

The adapter 30 is fastened to the threaded shaft 24 by means of a screw 31 passing through an axial hole 32 in the head member 30b and engaging a threaded hole 33 drilled in the cylindrical end 24a of the threaded shaft 24.

The function of adapter 30 is that of retaining means of the plunger head 14 even in case the plunger is attracted by the free flow liquid leaking from the syringe.

In order to accomplish the above mentioned function the adapter 30 provides for two characteristics co-operating in a synergetic manner:
a) the side surface 35 of the head member 30c in the adapter 30 is roughened for increasing its coefficient of friction;
b) the diameter of the neck portion 30b is smaller than that of the head member 30c so that the edge of the seat 14a in the plunger head 14 surrounds it, thus increasing the seal between the plunger 14 and said adapter 30.

The roughness of the side surface 35 of head member 30c can be accomplished in several ways, such as for example by gluing granules of suitable size or through machining.

In the preferred embodiment of the invention such roughness is accomplished through a knurling achieved by means of a pair of rolls angled to one another so as to generate a plurality of evenly spaced pyramidally shaped cusps 36.

The threading formed over the elastically deformable inner surface of the seat 14a of the plunger head 14 engages such cusps 36.

More particularly by comparing the FIGS. 2 and 4, the former illustrates how the seat 14a is affected by the deformation experienced by the plunger head 14 inserted into the syringe 12, and the latter shows the shape of such plunger when it is outside of the syringe (FIG. 4).

Such deformation is more appreciable near the outer end of the plunger 14 since the seat 14a diminishes the stiffness thereof.

Thanks to the elasticity of the plunger made of rubber and to the bevel 30"c, a syringe full of liquid can be easily inserted without causing movements of the plunger.

In fact, by slowly actuating the apparatus 1 with small alternate twists along the axis of the threaded shaft 24, the contact of the knurled head member 30c occurs on the inner threading formed on the surface of the seat 14a, thus allowing the insertion of the head member 30c of the adapter 30 without advancing the plunger 14.

Figure 6:
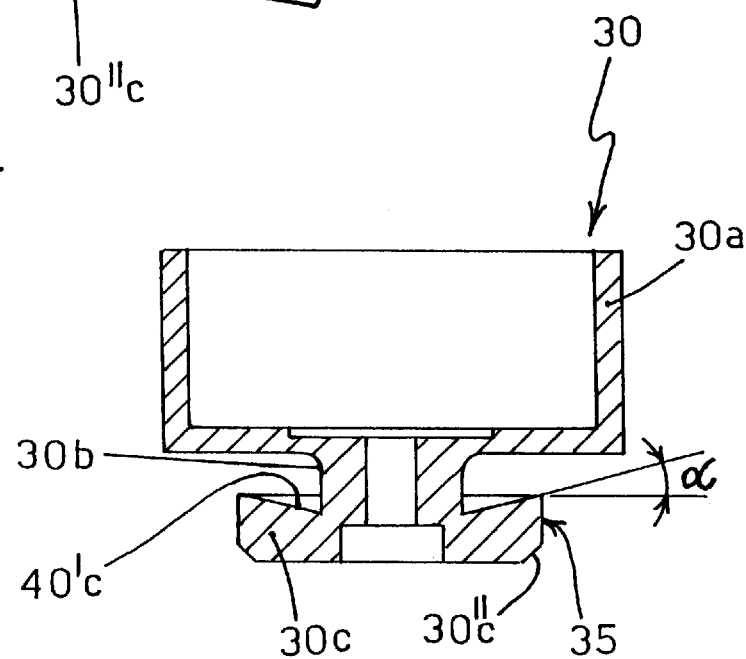
FIG. 6 is a front section view of a detail of the apparatus according to a different embodiment of the invention.

With reference to FIG. 6, according to another embodiment of the invention, in the adapter 30 the base 40'c of the head member 30c is beveled or tapered.

The tapering of the base 40'c is directed inwardly of the head member 30c of the adapter 30 and has an angle comprised between 15° and 45°, preferably 30°, with respect to the horizontal.

The adapter 30 according to this embodiment is more strongly embedded into the plunger head 14 since the much sharper edge of the head member 30c bites into the walls of the seat 14a of the plunger 14.

Advantageously inside the body 30a the adapter 30 carries an extendable sleeve or bellows 34, the other end of which is fastened to the cover 11, for insulating the threaded shaft 24—and therefore the inside of the apparatus 1—from the surrounding environment in order to prevent damages to the inner components of the apparatus caused by leakages of fluid from the syringe 12.

The bellows 34 will be accordion-like folded and housed within the recess formed in the body 30a after the threaded shaft 24 has been completely retracted.

When the threaded shaft 24 is extended the bellows 34 will spread out following the shaft motion.

What is claimed is:

1. An infusion apparatus for administering drugs to a patient through a syringe, said apparatus comprising:
a plunger head engaged in the syringe and having an internally threaded seat;
an axially moveable threaded shaft adapted to push the plunger head in the syringe; and
retaining means interposed between the shaft and the plunger head for retaining the plunger head, the retaining means being adapted to prevent an uncontrolled decent of the plunger head within the syringe and an associated effect of free flow and drug overdosing;
said retaining means comprising an adapter fastened to one end of the threaded shaft, the adapter comprising a hollow body, a cylindrical neck portion and a cylindrical head member having a side surface that is roughened, the neck portion and the head member being forceable fitted into the threaded seat of the plunger head for retaining the plunger head.

2. An infusion apparatus according to claim 1, wherein the head member has a substantially flat base which merges with the neck portion.

3. An infusion apparatus according to claim 1, wherein the head member has a tapered base which merges with the neck, the base tapering into the head member at an angle of 15° to 45° to the horizontal when the threaded shaft extends vertically.

4. An infusion apparatus according to claim 3, wherein the head member includes a tapered edge opposite from the base for facilitating entry of the head member into the seat of the plunger head.

5. An infusion apparatus according to claim 4, including a housing which is closed by a cover, the housing being operatively connected to the threaded shaft.

6. An infusion apparatus according to claim 5, including a bellows around the threaded shaft and extending from the hollow body of the adapter to the cover of the housing for protecting the apparatus from surrounding environment.

* * * * *